United States Patent [19]

Du et al.

[11] 4,439,606

[45] Mar. 27, 1984

[54] ANTIATHEROSCLEROTIC 1-PIPERAZINECARBONYL COMPOUNDS

[75] Inventors: Mila T. Du, Suffern, N.Y.; Robert G. Shepherd, Selbyville, Del.

[73] Assignee: American Cyanamid Company, Stamford, Conn.

[21] Appl. No.: 375,507

[22] Filed: May 6, 1982

[51] Int. Cl.$^3$ ............... C07D 403/04; C07D 401/04; C07D 401/06; A61K 31/491

[52] U.S. Cl. .................................. 544/356; 544/357; 544/360; 544/363; 544/367; 544/386; 424/250

[58] Field of Search ............................ 544/356, 357

[56] References Cited

PUBLICATIONS

Conroy et al., J. Am. Pharm. Asso. 625, 43, (1954).

Primary Examiner—Mark L. Berch
Assistant Examiner—C. C. Kalita
Attorney, Agent, or Firm—J. W. Richards

[57] ABSTRACT

This disclosure describes 4-aryl, -heteroaryl and -heteroarylmethyl-1-piperazinecarbonyl compounds which are capable of ameliorating atherosclerosis in mammals.

30 Claims, No Drawings

ANTIATHEROSCLEROTIC 1-PIPERAZINECARBONYL COMPOUNDS

BACKGROUND OF THE INVENTION

This invention is concerned with organic compounds which are useful as pharmaceutical agents. The compounds of the present invention are 1-piperazinecarbonyl compounds which are capable of ameliorating atherosclerosis in mammals. This invention further relates to novel 1-piperazinecarbonyl compounds and methods for the chemical synthesis of these compounds. The invention also relates to pharmaceutical compositions for the utilization of these compounds in the treatment of disease in mammals. The invention contemplates methods for treating atherosclerosis in a mammal in a manner designed to prevent, arrest, or reverse the course of the disease.

The specific compounds of this invention are 4-heteroaryl-1-piperazinecarbonyl, 4-aryl-1-piperazinecarbonyl, and 4-heteroarylmethyl-1-piperazinecarbonyl compounds and this invention contemplates as novel compounds per se only certain types of 1-piperazinecarbonyl compounds which are not known in the art. The following references disclose compounds which are structurally related to the new compounds of this invention but which are sufficiently different in chemical structure to be considered patentably distinct: Chemical Abstracts 28:1348[1]; 31:1949[2]; 32:570[5]; 33:2897[5]; 42:1942f; 48:13694; 56: 10143e; 68:87274t; and 84:4904e. None of the compounds disclosed in these references are reported or claimed to be useful for the treatment of atherosclerosis in mammals.

Atherosclerosis is a form of arteriosclerosis characterized by lipid accumulation in and thickening of the arterial walls of both medium and large-sized arteries. Arterial walls are thereby weakened and the elasticity and effective internal size of the artery is decreased. Atherosclerosis is the most common cause of coronary artery disease and is of great medical importance since the occlusion of medium and large-sized arteries diminishes the supply of blood to vital organs such as the heart muscles and the brain. The sequelae to atherosclerosis include ischemic heart disease, heart failure, life-threatening arrythmias, senility and stroke.

The fact that cholesterol is a major component of atherosclerotic lesions or plaques has been known for more than 100 years. Various researchers have studied the role of cholesterol in lesion formation and development and also, more importantly, whether lesion formation can be prevented or lesion development arrested or reversed. Atheromatous lesions have now been shown [Adams, et al., Atherosclerosis, 13, 429 (1974)] to contain a greater quantity of esterified as opposed to unesterified cholesterol than the surrounding undiseased arterial wall. The intracellular esterification of cholesterol with fatty acids is catalyzed by the enzyme "Fatty acyl CoA:-cholesterol acyl transferase" or ACAT and the accumulation and storage of cholesterol esters in the arterial wall is associated with increased activity of this enzyme [Hashimoto and Dayton, Atherosclerosis, 28, 447 (1977)]. In addition, cholesterol esters are removed from cells at a slower rate than unesterified cholesterol [Bondjers and Bjorkerud, Atherosclerosis, 15, 273 (1972) and 22, 379 (1975)]. Thus, inhibition of the ACAT enzyme would diminish the rate of cholesterol esterification, decrease the accumulation and storage of cholesterol esters in the arterial wall, and prevent or inhibit the formation and development of atheromatous lesions. The compounds of the present invention are very potent inhibitors of the ACAT enzyme. Thus, these compounds are useful for controlling and reducing the cholesterol ester content of mammalian arterial walls and decreasing the accumulation and storage of cholesterol in the arterial walls of mammals. Further, the compounds of this invention inhibit the formation or development of atherosclerotic lesions in mammals.

The evidence that hyperlipidemia is one of the factors involved in coronary heart disease is very impressive. A most important study carried out in Framingham, Mass. (Gordon and Verter, 1969) in over 5,000 persons for more than 12 years established a correlation between high concentrations of blood cholesterol and increased risk of heart attack. Although the causes of coronary artery disease are multiple, one of the most constant factors has been the elevated concentration of lipids in the blood plasma. A combined elevation of cholesterol and triglycerides has been shown (Carlson and Bottiger, 1972) to carry the highest risk of coronary heart disease. The majority of patients with ischemic heart disease or peripheral vascular disease were found to have hyperlipoproteinemia, involving very low-density and/or low-density lipoproteins (Lewis, et al., 1974).

We have now found that certain members of this class of compounds can safely and effectively lower serum lipids in warm-blooded animals. Such action on serum lipids is considered to be very useful in the treatment of atherosclerosis. For some time it has been considered desirable to lower serum-lipid levels and to correct lipo-protein imbalance in mammals as a preventive measure against atherosclerosis. The compounds of the present invention do not act by blocking late stages of cholesterol biosynthesis and thus do not produce accumulation of intermediates such as desmosterol, as equally undesirable as cholesterol itself. Compounds with the combination of therapeutically favorable characteristics possessed by those of the present invention can be safely administered to warm-blooded mammals for the treatment of hyperlipidemic and atherosclerotic states found in patients with or prone to heart attacks, to peripheral or cerebral vascular disease, and to stroke.

The compounds of this invention exhibit anti-atherosclerotic activity and the invention should not be construed as limited to any particular mechanism of anti-atherosclerotic action.

SUMMARY OF THE INVENTION

This invention relates to new organic compounds, their preparation, pharmaceutical compositions containing them, and their use in the treatment of atherosclerosis. More particularly, it is concerned with novel 1-piperazinecarbonyl compounds which may be represented by the formula:

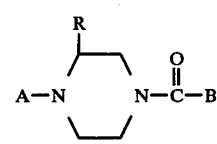

wherein A is selected from the group consisting of 2-pyrazinyl, 2-quinoxalinyl, 2-quinolyl, p-chlorophenyl, 3-pyridylmethyl, 2-thiazolyl and 6-methoxy-2-pyrazinyl; B is selected from the group comprising phenyl, mono- and polysubstituted phenyl [wherein the substituents may be fluoro, alkyl ($C_1$-$C_4$), or trifluoromethyl], benzyl, mono- and disubstituted benzyl [wherein the substituents may be chloro, nitro or alkyl ($C_1$-$C_3$)], alkyl ($C_1$-$C_7$), cycloalkyl ($C_3$-$C_6$), pyridyl, 2-phenoxypropionyl, alkyl($C_1$-$C_4$) amino, polyfluoro($F_7$-$F_{14}$)-alkyl($C_3$-$C_7$), mono- and disubstituted phenylamino (wherein the substituents may be chloro, carboxylic acid or ethyl carboxylate), 6-p-chlorophenylhexyl, 5-(p-chlorobenzoyl)butyl, 2-p-chlorophenoxy-2-isopropyl and 1-methylbenzyl; and R is selected from the group comprising hydrogen and alkyl ($C_1$-$C_3$).

This invention is further concerned with methods for treating atherosclerosis in a mammal with 1-piperazinecarbonyl compounds which may be represented by the formula:

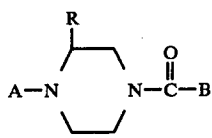

II wherein R and B are as described above and A, in addition to being as described above, may be unsubstituted phenyl.

This invention also relates to a method of reducing the cholesterol content of the arterial walls of mammals which comprises administering to said mammal an effective amount of a compound of formula II above.

This invention also relates to a method of treating hyperlipidemia in a mammal which comprises administering to said mammal an effective amount of a compound of formula II above.

This invention also relates to a method of inhibiting atherosclerotic lesion development in a mammal which comprises administering to said mammal an effective amount of a compound of formula II above.

This invention still further relates to a pharmaceutical composition which comprises an effective anti-atherosclerotic amount of a compound of formula II above in association with a pharmaceutically acceptable carrier.

Finally, this invention relates to chemical processes for preparing the novel compounds of formula I above. These processes are disclosed more completely in the detailed description of the invention below.

Preferred embodiments of the invention involve compounds of formula I in which A is 2-pyrazinyl, 2-quinolyl, or 4-chlorophenyl group. More preferred embodiments involve compounds of formula I in which A is a 2-pyrazinyl, 2-quinolyl, or 4-chlorophenyl group and R is hydrogen or methyl. The most preferred embodiments involve compounds of formula I in which A is a 2-pyrazinyl, 2-quinolyl, or 4-chlorophenyl group; R is hydrogen or methyl, and B is mono- or disubstituted benzyl. Specific preferred embodiments of the invention involve the compounds:

1-(p-chlorophenyl)-4-phenylacetylpiperazine,
1-(p-chlorophenyl)-2-methyl-4-phenylacetylpiperazine,
1-(2-quinolyl)-4-phenylacetylpiperazine,
1-[6-(p-chlorophenyl)hexanoyl]-4-(2-pyrazinyl)piperazine,
1-(pentadecafluorooctanoyl)-4-(2-pyrazinyl)piperazine,
1-(o-methylphenylacetyl)-4-(2-pyrazinyl)piperazine,
1-(2-pyrazinyl)-4-(p-tolylacetyl)piperazine,
1-(3,4-dichlorophenylacetyl)-4-(2-pyrazinyl)piperazine,
1-(2-pyrazinyl)-4-($\alpha,\alpha,\alpha$-trifluoro-o-toluoyl)piperazine, and 1-(p-nitrophenylacetyl)-4-(2-pyrazinyl)piperazine.

DETAILED DESCRIPTION OF THE INVENTION

The compounds of this invention may be prepared by one of the following procedures:

(A) An appropriately substituted phenylacetyl derivative and thionyl chloride in methylene chloride is refluxed for 1-2 hours, then the solvent is evaporated. The residue is dissolved in benzene and added dropwise to a solution of 1-(2-pyrazinyl)piperazine and triethylamine in benzene. This mixture is refluxed for 1-2 hours, filtered while hot, extracted with dilute alkali and evaporated giving the products of Examples 1-11, 35 and 36.

(B) A 2-(1-piperazinyl)aryl derivatives and triethylamine in benzene are added dropwise to a solution of phenylacetylchloride in benzene and refluxed for 1-2 hours. Evaporation and recrystallization from benzene gives the products of Examples 12-26 and 37.

(C) An appropriately substituted phenylisocyanate in solution in ether is added dropwise to a solution of 1-(2-pyrazinyl)piperazine in ether and stirred for 1-2 hours giving the products of Examples 27-32.

The 1-piperazinecarbonyl compounds of the present invention are obtained as crystalline solids or distillable liquids. They are characterized by distinct melting or boiling points and unique spectra. They are appreciably soluble in organic solvents but generally less soluble in water. The preparation and properties of the compounds of this invention will be described in greater detail in conjunction with the examples shown below.

The compounds of the present invention were tested for their ability to inhibit the enzymatic esterification of cholesterol according to the procedure of Hashimoto, et al., Life Sci., 12(Part II), 1-12 (1973).

Rat adrenals were homogenized in 0.2 M monobasic potassium phosphate buffer, pH 7.4, and centrifuged at 1000 times gravity for 15 minutes at 5° C. The supernatant, containing the microsomal fraction, served as the source of the cholesterol-esterifying enzyme, fatty acyl CoA:-cholesterol acyl transferase (ACAT). A mixture comprising 50 parts of adrenal supernatant, 10 parts of bovine serum albumin (50 mg./ml.), 3 parts of test compound (final concentration 5.2 $\mu$g./ml.) and 500 parts of buffer were preincubated at 37° C. for 10 minutes, following which 20 parts of oleoyl CoA($^{17}$C-0.4 $\mu$Ci) were added and the final mixture was incubated at 37° C. for 30 minutes. A control mixture, omitting the test compound, was prepared and treated in the same manner. The lipids from the incubation mixture were extracted into an organic solvent and separated by thin-layer chromatography. The cholesterol ester fraction was counted in a scintillation counter. A statistically significant inhibition of the ACAT enzyme is the criterion for activity.

The results of this test on representative compounds of this invention appear in Table I.

TABLE I

| Compound | % Inhibition |
|---|---|
| 1-(2-phenoxypropionyl)-4-(2-pyrazinyl)-piperazine | 30.5 |
| 1-phenylacetyl-4-(2-quinoxalinyl)-piperazine | 40.1 |
| 1-(p-tert.-butylbenzoyl)-4-(2-pyrazinyl)piperazine | 39.7 |

TABLE I-continued

| Compound | % Inhibition |
|---|---|
| 1-octanoyl-4-(2-pyrazinyl)piperazine | 33.6 |
| 1-(2,4-dichlorophenylacetyl)-4-(2-pyrazinyl)piperazine | 32.2 |
| 1-(p-chlorophenyl)-4-phenylacetylpiperazine | 73.3 |
| 1-(3,4-dichlorophenylacetyl)-4-(2-pyrazinyl)piperazine | 38.3 |
| 1-phenyl-4-phenylacetylpiperazine | 34.6 |
| 1-(p-nitrophenylacetyl)-4-(2-pyrazinyl)piperazine | 36.4 |
| 1-(p-chlorophenyl)-2-methyl-4-phenylacetylpiperazine | 88.1 |
| 1-pentafluorobenzoyl-4-(2-pyrazinyl)piperazine | 31.2 |
| N—tert.-butyl-4-(2-pyrazinyl)-1-piperazinecarboxamide | 35.4 |
| ethyl-p-[4-(2-pyrazinyl)-1-piperazinecarboxamido]benzoate | 42.2 |
| 1-(2-thiazolyl)-4-o-tolylacetylpiperazine | 32.6 |
| 1-phenylacetyl-4-(2-quinolyl)piperazine | 89.7 |
| 1-[5-(p-chlorobenzoyl)valeryl]-4-(2-pyrazinyl)piperazine | 47.4 |
| 1-[2-(p-chlorophenoxy)-2-methylpropionyl]-4-(2-pyrazinyl)piperazine | 54.1 |
| p-[4-(2-pyrazinyl)-1-piperazinecarboxamido]benzoic acid | 30.6 |
| 1-(pentadecafluorooctanoyl)-4-(2-pyrazinyl)piperazine | 39.0 |
| 1-(6-methoxy-2-pyrazinyl)-4-phenylacetylpiperazine | 38.1 |
| 1-[6-(p-chlorophenyl)hexanoyl]-4-(2-pyrazinyl)piperazine | 68.9 |

The compounds were also tested for their ability to lower lipid levels in mammals. The compounds were administered orally admixed with diet to groups of four male rats COBS, CD, SD strain from Charles River Breeding Laboratories, Inc., Wilmington, Mass. A control group of eight rats was maintained on the diet alone; test groups were maintained on the diet plus 0.1% of test compound by weight. After 5 days treatment, serum cholesterol and triglyceride concentrations were determined by direct enzymatic procedures using a Centrifichem ® System 400 autoanalyzer (Union Carbide Co.). Cholesterol concentrations were determined by the combined cholesterol esterasecholesterol oxidase procedure of Roeschlau, et al., Zeit. Klin. Chem. Klin. Biochem., 12, 226 (1974). Triglycerides were determined by the combined method of lipase catalyzed hydrolysis of triglycerides to glycerol and free fatty acids [Bucolo, G. and David, H., Clin. Chem., 19, 476 (1973) and Wahlefeld, A. W., in "Methods of Enzymatic Analysis," Vol, 4, Bergmeyer, H. D., Editor, Academic Press, New York, N.Y. (1974), pp. 1831–1835] and the enzymatic oxidation of the glycerol which leads to the production of colored formazan [Stavropoulos, W. S. and Crouch, R. D., Clin. Chem., 20, No. 7, 857 (1974)]. Changes in serum lipids are expressed as percent lowering from the values in control animals which did not receive drug treatment. The results of this test on representative animals appear in Table II. The compounds are considered active if they produce a statistically significant lowering of either sterol or triglycerides.

TABLE II

| Compound | % Lowering of Serum | |
|---|---|---|
|  | Sterol | Triglycerides |
| 1-(m-chlorophenylacetyl)-4-(2-pyrazinyl)piperazine |  | 46 |
| 1-(pentadecafluorooctanoyl)-4-(2-pyrazinyl)piperazine | 47 | 74 |
| 1-(2-phenoxypropionyl)-4-(2-pyrazinyl)piperazine |  | 62 |
| 1-(2-pyrazinyl)-4-(3-pyridylcarbonyl)piperazine |  | 30 |
| 1-(2,4-dichlorophenylacetyl)-4-(2-pyrazinyl)piperazine |  | 44 |
| 1-(2-pyrazinyl)-4-(p-tolylacetyl)piperazine |  | 49 |
| 1-(2-pyrazinyl)-4-(m-tolylacetyl)piperazine |  | 40 |
| 1-(2-methylphenylacetyl)-4-(2-pyrazinyl)piperazine |  | 55 |
| 1-(p-chlorophenyl)-2-methyl-4-phenylacetylpiperazine |  | 61 |
| 1-(p-chlorophenylacetyl)-4-(2-pyrazinyl)piperazine |  | 51 |
| 1-phenylacetyl-4-(3-pyridylmethyl)piperazine |  | 34 |
| N—ethyl-4-(2-pyrazinyl)-1-piperazinecarboxamide |  | 43 |
| N—methyl-4-(2-pyrazinyl)-1-piperazinecarboxamide |  | 38 |
| 4'-chloro-4-(2-pyrazinyl)-1-piperazinecarboxanilide |  | 33 |
| 1-benzoyl-4-(2-pyrazinyl)piperazine |  | 30 |
| 1-heptafluorobutyroyl-4-(2-pyrazinyl)piperazine |  | 51 |
| 1-cyclopropylcarbonyl-4-(2-pyrazinyl)piperazine |  | 37 |
| 1-phenylacetyl-4-(2-quinolyl)piperazine | 69 | 53 |
| 1-[5-(p-chlorobenzoyl)valeryl]-4-(2-pyrazinyl)piperazine |  | 45 |
| 1-[2-(p-chlorophenoxy)-2-methylpropionyl]-4-(2-pyrazinyl)piperazine |  | 42 |
| 1-(6-methoxy-2-pyrazinyl)-4-phenylacetylpiperazine |  | 56 |
| 1-[6-(p-chlorophenyl)hexanoyl]-4-(2-pyrazinyl)piperazine |  | 30 |

The compounds were further tested for their ability to decrease aortic sterol content without effecting serum sterol.

Day-old Cockerels were placed on diets consisting of pullet starter mash supplemented with either 20 g. cholesterol (control group) or 20 g. cholesterol and 525 mg. test compound (drug-treated group) per kg. of diet.

For the control diet, 20 g. of cholesterol was dissolved in 200 ml. of chloroform, mixed into one kg. of pullet starter mash and then the choloroform was removed by evaporation.

For the drug-treatment group, 525 mg. of the test compound was dissolved in 100 ml. of chloroform, mixed into a diet prepared as described above and then the chloroform was evaporated.

The cockerels were housed three per cage and given water and their respective diet ad libitum for 14 days. Blood was collected by cardiac puncture and the serum was saponified [Trinder, P., Analyst, 77, 321 (1952)] and extracted and the cholesterol content determinted [Zlatkis, A., et al., J. Lab Clin Med., 41 486 (1953)]. The aortae were removed, cleaned of adventitial tissue and the sterol content determined according to the above procedures. Compounds which statistically decrease the aortic sterol content without having an effect on serum sterol are considered to be active. The results of this test on representative compounds of this invention appear in Table III.

TABLE III

| Compound | Result |
| --- | --- |
| 1-(o-methylphenylacetyl)-4-(2-pyrazinyl)-piperazine | Active |
| 1-(2-pyrazinyl)-4-(p-tolylacetyl)piperazine | Active |
| 1-(3,4-dichlorophenylacetyl)-4-(2-pyrazinyl)-piperazine | Active |
| 1-(2-pyrazinyl)-4-($\alpha,\alpha,\alpha$-trifluoro-o-toluoyl)piperazine | Active |
| 1-phenyl-4-phenylacetyl piperazine | Active |
| 1-(p-nitrophenylacetyl)-4-(2-pyrazinyl)-piperazine | Active |
| 2',6'-dichloro-4-(2-pyrazinyl)-1-piperazine-carboxanilide | Active |

When the compounds are employed for the above utility, they may be combined with one or more pharmaceutically acceptable carriers, e.g., solvents, diluents and the like, and may be administered orally in such forms as tablets, capsules, dispersible powders, granules, suspensions containing, for example, from about 0.5 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.5 to 5% suspending agent in an isotonic medium. These pharmaceutical preparations may contain, for example, from about 0.5 up to about 90% of the active ingredient in combination with the carrier, more usually between 5 and 60% by weight.

The antiatherosclerotic effective dosage of active ingredient employed for the reduction of cholesterol ester content in the arterial walls of a mammal may vary depending on the particular compound employed, the mode of administration and the severity of the condition being treated. However, in general, satisfactory results are obtained when the compounds of the invention are administered at a daily dosage of from about 2 mg. to about 500 mg. per kg. of animal body weight, preferably given in divided doses two to four times a day, or in sustained release form. For most large mammals, the total daily dosage is from about 100 mg. to about 5,000 mg. preferably from about 100 mg. to 2,000 mg. Dosage forms suitable for internal use comprise from about 25 to 500 mg. of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. A decided practical advantage is that these active compounds may be administered orally as well as by intravenous, intramuscular, or subcutaneous routes if necessary. Solid carriers include starch, lactose, dicalcium phosphate, microcrystalline cellulose, sucrose and kaolin, while liquid carriers include sterile water polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, e.g., vitamin E, ascorbic acid, BHT and BHA.

The preferred pharmaceutical compositions from the stand-point of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The invention will be more fully described in conjunction with the following specific examples which are not to be construed as limiting the scope of the invention.

EXAMPLE 1

1-(2,4-Dichlorophenylacetyl)-4-(2-pyrazinyl)piperazine

A solution of 6.15 g. of 2,4-dichlorophenylacetic acid and 22.0 ml. of thionyl chloride in 20 ml. of methylenechloride was refluxed for one hour. The solvent was evaporated and a solution of the residue in 30 ml. of benzene was added dropwise with stirring to a solution of 4.92 g. of 1-(2-pyrazinyl)piperazine and 3.80 g. of triethylamine in 60 ml. of benzene. The mixture was refluxed for one hour then filtered while hot. The filtrate was extracted with dilute sodium hydroxide, washed with water, dried, evaporated and recrystallized from ethanol, giving 7.43 g. of the desired product, m.p. 124°–125° C.

The products listed as Examples 2–11 in Table IV were prepared by the procedure of Example 1, employing appropriate starting materials.

TABLE IV

| Example | Name | M.P. °C. |
| --- | --- | --- |
| 2 | 1-(m-Chlorophenylacetyl)-4-(2-pyrazinyl)-piperazine | 84–86 |
| 3 | 1-(o-Methylphenylacetyl)-4-(2-pyrazinyl)-piperazine | 92–94 |
| 4 | 1-(2-Pyrazinyl)-4-(p-tolylacetyl)piperazine | 82–83 |
| 5 | 1-(3,4-Dichlorophenylacetyl)-4-(2-pyrazinyl)piperazine | 125–126 |
| 6 | 1-(2-Pyrazinyl)-4-(m-tolylacetyl)piperazine | 88–89 |
| 7 | 1-(p-Nitrophenylacetyl)-4-(2-pyrazinyl)-piperazine | 124–126 |
| 8 | 1-(2-Methylphenylacetyl)-4-(2-pyrazinyl)-piperazine | 95–96 |
| 9 | 1-(p-Chlorophenylacetyl)-4-(2-pyrazinyl)-piperazine | 130–132 |
| 10 | 1-Heptafluorobutyroyl-4-(2-pyrazinyl)-piperazine | oil |

TABLE IV-continued

| Example | Name | M.P. °C. |
|---|---|---|
| 11 | 1-[2-(p-Chlorophenoxy)-2-methylpropionyl]-4-(2-pyrazinyl)piperazine | 99–100 |

EXAMPLE 12

1-Phenylacetyl-4-(2-quinoxalinyl)piperazine

To a solution of 6.42 g. of 2-(1-piperazinyl)-quinoxaline and 3.65 g. of triethylamine in 60 ml. of benzene was added dropwise with stirring a solution of 4.64 g. of phenylacetylchloride in 30 ml. of benzene. The mixture was refluxed for one hour, then filtered while hot. Evaporation of the filtrate and recrystallization from benzene gave 5.2 g. of the desired product, m.p. 156°–158° C.

The products listed as Examples 13–26 in Table V were prepared by the procedure of Example 12, employing appropriate starting materials.

TABLE V

| Example | Name | M.P. °C. |
|---|---|---|
| 13 | 1-(2-Phenoxypropionyl)-4-(2-pyrazinyl)piperazine | 114–115 |
| 14 | 1-(p-tert.-Butylbenzoyl)-4-(2-pyrazinyl)piperazine | 140–141 |
| 15 | 1-Octanoyl-4-(2-pyrazinyl)piperazine | 72–73 |
| 16 | 1-(2-Pyrazinyl)-4-(3-pyridylcarbonyl)piperazine | 87–89 |
| 17 | 1-(2-Pyrazinyl)-4-(α,α,α-trifluoro-o-toluoyl)piperazine | 123–124 |
| 18 | 1-Phenyl-4-phenylacetylpiperazine | 93–94 |
| 19 | 1-(p-Chlorophenyl)-2-methyl-4-phenylacetylpiperazine | 122–123 |
| 20 | 1-Phenylacetyl-4-(3-pyridylmethyl)piperazine | oil |
| 21 | 1-Benzoyl-4-(2-pyrazinyl)piperazine | 109–111 |
| 22 | 1-Cyclopropylcarbonyl-4-(2-pyrazinyl)piperazine | 94–95 |
| 23 | 1-Pentafluorobenzoyl-4-(2-pyrazinyl)piperazine | 120–121 |
| 24 | 1-Phenylacetyl-4-(2-quinolyl)piperazine | 135–138 |
| 25 | 1-(Pentadecafluorooctanoyl)-4-(2-pyrazinyl)piperazine | 82–84 |
| 26 | 1-(6-Methoxy-2-pyrazinyl)-4-phenylacetylpiperazine | 133–135 |

EXAMPLE 27

2',6'-Dichloro-4-(2-pyrazinyl)-1-piperazinecarboxanilide

A solution of 1.88 g. of 2,6-dichlorophenylisocyanate in 25 ml. of anhydrous ether was added dropwise to a stirred solution of 1.64 g. of 1-(2-pyrazinyl)piperazine in 250 ml. of anhydrous ether. The mixture was stirred for 30 minutes and the solid was collected and recrystallized from ethanol, giving 3.12 g. of the desired product, m.p. 177°–179° C.

The products listed as Examples 28–32 in Table VI were prepared by the procedure of Example 27, employing appropriate starting materials.

TABLE VI

| Example | Name | M.P. °C. |
|---|---|---|
| 28 | N—Ethyl-4-(2-pyrazinyl)-1-piperazinecarboxamide | 169.5–171.5 |
| 29 | N—Methyl-4-(2-pyrazinyl)-1-piperazinecarboxamide | 120–122 |
| 30 | 4'-Chloro-4-(2-pyrazinyl)-1-piperazinecarboxanilide | 155–157 |
| 31 | N—tert.-Butyl-4-(2-pyrazinyl)-1-piperazinecarboxamide | 201–203 |

TABLE VI-continued

| Example | Name | M.P. °C. |
|---|---|---|
| 32 | Ethyl-p-[4-(2-pyrazinyl)-1-piperazinecarboxamido]benzoate | 163–165 |

EXAMPLE 33

1-(p-Chlorophenyl)-4-phenylacetylpiperazine

To a cold solution of 8.09 g. of p-chlorophenyl piperazine dihydrochloride and 40 ml. of 10% sodium hydroxide in 60 ml. of water was added dropwise with stirring, 4.64 g. of phenylacetyl chloride. The mixture was stirred for one hour, then neutralized with 2 N hydrochloric acid. The solid was collected and recrystallized from ethanol-water, giving 4.2 g. of the desired product, m.p. 93°–94° C.

EXAMPLE 34 p-[4-(2-Pyrazinyl)-1-piperazinecarboxamide]-benzoic acid

A solution of 6.69 g. of ethyl p-[4-(2-pyrazinyl)-1-piperazinecarboxamido]benzoate and 1.32 g. of potassium hydroxide in 90 ml. of 80% ethanol was refluxed for 18 hours. The mixture was cooled and diluted with 90 ml. of water, then acidified with concentrated hydrochloric acid. The solid was collected and recrystallized from isopropanol, giving 3.5 g. of the desired product, m.p. 243°–245° C.

EXAMPLE 35

1-(2-Thiazolyl)-4-o-tolylacetylpiperazine

A mixture of 20.5 g. of 2-bromothiazole, 15.0 g. of anhydrous piperazine, 15.0 g. of sodium carbonate and 30 ml. of amyl alcohol was heated at reflux for 4 hours, then allowed to stand at ambient temperature for 48 hours, and filtered. The filtrate was extracted with four 10 ml. portions of 3 N hydrochloric acid. The extracts were combined and the aqueous layer made basic with 10 N sodium hydroxide to pH 12–13. The mixture was filtered and the filtrate extracted with three 50 ml. portions of chloroform. These extracts were combined, dried and concentrated in vacuo to a yellow oil. This oil was distilled on a Kugelrohr apparatus at 90° C./20μ, giving 16.79 g. of 1-(2-thiazolyl)piperazine as a colorless oil.

The 1-(2-thiazolyl)piperazine was converted to the desired product in 57% yield, by the procedure of Example 1 using the appropriate starting material, upon recrystallization from ethanol, m.p. 110°–111° C.

EXAMPLE 36

1-[5-(p-Chlorobenzoyl)valeryl]-4-(2-pyrazinyl)piperazine 5-p-Chlorobenzoylvaleric acid [L. F. Fieser, et al., J. Am. Chem. Soc., 70, 3197 (1948)] was reacted as described in Example 1, giving 74% yield of the desired product when recrystallized from ethanol, m.p. 138°–140° C.

EXAMPLE 37

1-[6-(p-Chlorophenyl)hexanoyl]-4-(2-pyrazinyl)piperazine

To a solution of 101 g. of ethyl adipate in 500 ml. of benzene was slowly added 120 ml. of thionyl chloride. The mixture was refluxed 4.5 hours, cooled and evaporated. The residue was evaporated three times from 500 ml. of benzene, giving 113 g. of yellow liquid.

A mixture of 155 g. of aluminum chloride, 200 ml. of dichloromethane and 77 ml. of p-chlorophenol was cooled to 3° C. in an ice-water bath. The above 113 g. of yellow liquid was added slowly with stirring over a period of 3 hours while the temperature was maintained at less than 5° C. The mixture ws refrigerated overnight, then warmed to 50° C., stirred for one hour and poured slowly into 1.5 liters of ice-water containing 200 ml. of 37% hydrochloric acid. The resulting oil was collected and evaporated giving 159.1 g. of tan solid. To a solution of this solid in 400 ml. of ethanol was slowly added 80 g. of 85% potassium hydroxide. After standing ½ hour, 100 ml. of water was added, the solution was stirred and refluxed for 2 hours, then cooled and evaporated. The residue was dissolved in one liter of water, adjusted to pH 1 with 37% hydrochloric acid and the solid was collected and recrystallized twice from ethanol giving 69.5 g. of orange solid.

A 55 g. portion of zinc was combined with 5.4 g. of mercuric chloride, 90 ml. of water and 3 ml. of concentrated hydrochloric acid. To this new sequentially added 35 ml. of water. 80 ml. of 37% hydrochloric acid, 45 ml. of toluene and 35 g. of the above orange solid. The reaction was brought to reflux for 24 hours, with 25 ml. portions of 37% hydrochloric acid added at 6 hour intervals. The reaction was cooled, diluted with water and the organic layer separated and distilled on a Kugelrohr apparatus giving (138°–142° C./50μ) 26.3 g. of colorless liquid. This liquid was hydrogenated with palladium on carbon catalyst giving 25.2 g. of colorless liquid which was again saponified giving 22.6 g. of colorless liquid. A solution of 15 g. of this liquid and 14 ml. of sulfonyl chloride in 200 ml. of benzene was refluxed for 6 hours, cooled, evaporated and extracted with three 200 ml. portions of benzene, giving 16.7 g. of 6-(p-chlorophenyl)hexanoyl chloride as an orange oil.

The 6-(p-chlorophenyl)hexanoyl chloride was reacted as described in Example 12 giving a 70% yield of the desired product when recrystallized from ethyl acetate, m.p. 88°–89° C.

We claim:

1. A compound selected from those of the formula

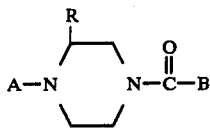

wherein A is selected from the group consisting of 2-pyrazinyl, 2-quinoxalinyl; B is selected from the group consisting of phenyl, mono- and polysubstituted phenyl (wherein the substituents may be fluoro, alkyl ($C_1$–$C_4$), or trifluoromethyl), benzyl, mono- and disubstituted benzyl (wherein the substituents may be chloro, nitro or alkyl ($C_1$–$C_3$) alkyl ($C_1$–$C_4$), cycloalkyl ($C_3$–$C_6$), pyridyl, 2-phenoxypropionyl, (alkyl ($C_1$–$C_4$)amino,) polyfluoro($F_7$–$F_{14}$)-alkyl($C_3$–$C_7$), mono- and disubstituted phenylamino (wherein the substituents may be chloro, carboxylic acid or ethyl carboxylate), 6-p-chlorophenylhexyl, 5-(p-chlorobenzoyl)butyl, 2-p-chlorophenoxy-2-isopropyl and 1-methylbenzyl; and R is selected from the group comprising hydrogen and alkyl ($C_1$–$C_3$).

2. The compound according to claim 1, 1-(2,4-dichlorophenylacetyl)-4-(2-pyrazinyl)piperazine.

3. The compound according to claim 1, 1-(m-chlorophenylacetyl)-4-(2-pyrazinyl)piperazine.

4. The compound according to claim , 1-(o-methylphenylacetyl)-4-(2-pyrazinyl)piperazine.

5. The compound according to claim 1, 1-(2-pyrazinyl)-4-(p-tolylacetyl)piperazine.

6. The compound according to claim 1, 1-(3,4-dichlorophenylacetyl)-4-(2-pyrazinyl)piperazine.

7. The compound according to claim 1, 1-(2-pyrazinyl)-4-(m-tolylacetyl)piperazine.

8. The compound according to claim 1, 1-(p-nitrophenylacetyl)-4-(2-pyrazinyl)piperazine.

9. The compound according to claim 1, 1-(2-methylphenylacetyl)-4-(2-pyrazinyl)piperazine.

10. The compound according to claim 1, 1-(p-chlorophenylacetyl)-4-(2-pyrazinyl)piperazine.

11. The compound according to claim 1, 1-heptafluorobutyroyl-4-(2-pyrazinyl)piperazine.

12. The compound according to claim 1, 1-[2-(p-chlorophenoxy)-2-methylpropionyl]-4-(2-pyrazinyl)piperazine.

13. The compound according to claim 1, 1-phenylacetyl-4-(2-quinoxalinyl)piperazine.

14. The compound according to claim 1, 1-(2-phenoxypropionyl)-4-(2-pyrazinyl)piperazine.

15. The compound according to claim 1, 1-(p-tert.-butylbenzoyl)-4-(2-pyrazinyl)piperazine.

16. The compound according to claim 1, 1-octanoyl-4-(2-pyrazinyl)piperazine.

17. The compound according to claim 1, 1-(2-pyrazinyl)-4-(3-pyridylcarbonyl)piperazine.

18. The compound according to claim 1, 1-(2-pyrazinyl)-4-(α,α,α-trifluoro-o-toluoyl)piperazine.

19. The compound according to claim 1, 1-benzoyl-4-(2-pyrazinyl)piperazine.

20. The compound according to claim 1, 1-cyclopropylcarbonyl-4-(2-pyrazinyl)piperazine.

21. The compound according to claim 1, 1-pentafluorobenzoyl-4-(2-pyrazinyl)piperazine.

22. The compound according to claim 1, 1-(pentadecafluorooctanoyl)-4-(2-pyrazinyl)piperazine.

23. The comppound according to claim 1, 1-(6-methoxy-2-pyrazinyl)-4-phenylacetylpiperazine.

24. The compound according to claim 1, 2′,6′-dichloro-4-(2-pyrazinyl)-1-piperazinecarboxanilide.

25. The compound according to claim 1, 4′-chloro-4-(2-pyrazinyl)-1-piperazinecarboxanilide.

26. The compound according to claim 1, N-tert.-butyl-4-(2-pyrazinyl)-1-piperazinecarboxanilide.

27. The compound according to claim 1, ethyl-p-[4-(2-pyrazinyl)-1-piperazinecarboxamido[benzoate.

28. The compound according to claim 1, p-[4-(2-pyrazinyl)-1-piperazinecarboxamido]benzoic acid.

29. The compound according to claim 1, 1-[5-(p-chlorobenzoyl)valeryl]-4-(2-pyrazinyl)piperazine.

30. The compound according to claim 1, 1-[6-(p-chlorophenyl)hexanoyl]-4-(2-pyrazinyl)piperazine.

* * * * *